(12) United States Patent
Brown et al.

(10) Patent No.: US 9,510,812 B2
(45) Date of Patent: Dec. 6, 2016

(54) TELESCOPING SURGICAL SUPPORT AND RETRACTOR SYSTEM

(75) Inventors: Jerry M. Brown, Sewaren, NJ (US); Adrian Greda, Harwood Heights, IL (US); Krzysztof S. Kubala, Wheeling, IL (US)

(73) Assignee: AUTOMATED MEDICAL PRODUCTS CORPORATION, Sewaren, NJ (US)

( * ) Notice: Subject to any disclaimer, the term of this patent is extended or adjusted under 35 U.S.C. 154(b) by 1015 days.

(21) Appl. No.: 13/475,837

(22) Filed: May 18, 2012

(65) Prior Publication Data

US 2013/0023735 A1 Jan. 24, 2013

Related U.S. Application Data

(60) Provisional application No. 61/487,593, filed on May 18, 2011.

(51) Int. Cl.
*A61B 17/02* (2006.01)
*A61B 17/00* (2006.01)
*A61B 17/30* (2006.01)

(52) U.S. Cl.
CPC .............. *A61B 17/02* (2013.01); *A61B 90/50* (2016.02); *A61B 2017/00057* (2013.01); *A61B 2017/00991* (2013.01); *A61B 2017/306* (2013.01); *A61B 2090/571* (2016.02)

(58) Field of Classification Search
CPC . A61B 17/02; A61B 17/0206; A61B 17/0212; A61B 17/0293; A61B 17/0281; A61B 2019/267; A61B 2019/268; A61B 2017/00991; A61B 2017/00407
See application file for complete search history.

(56) References Cited

U.S. PATENT DOCUMENTS

| | | | | |
|---|---|---|---|---|
| 3,910,538 A | * | 10/1975 | Baitella | F16M 11/14 248/124.1 |
| 4,143,652 A | * | 3/1979 | Meier | A61B 17/02 600/203 |
| 4,491,435 A | * | 1/1985 | Meier | F16C 11/106 248/276.1 |
| 4,796,846 A | | 1/1989 | Meier et al. | |
| 4,863,133 A | * | 9/1989 | Bonnell | A61B 19/26 16/319 |
| 5,667,481 A | * | 9/1997 | Villalta | A61B 17/02 600/219 |
| 5,976,171 A | * | 11/1999 | Taylor | A61B 17/0206 600/201 |
| 6,302,843 B1 | * | 10/2001 | Lees | A61B 17/02 600/228 |
| 6,315,260 B1 | | 11/2001 | Lees | |

(Continued)

*Primary Examiner* — Mary Hoffman
(74) *Attorney, Agent, or Firm* — Dorsey & Whitney LLP

(57) ABSTRACT

The surgical support system may include a primary telescoping support, secondary telescoping support supported from the primary telescoping support and configured for telescopically mounting a surgical tool thereto, such that telescoping of the primary support repositions the secondary telescoping support; and a positioning joint disposed between the primary and secondary telescoping supports for universally positioning and locking the secondary telescoping support with respecting to the primary telescoping support.

18 Claims, 17 Drawing Sheets

(56) References Cited

U.S. PATENT DOCUMENTS

| | | | |
|---|---|---|---|
| 6,387,047 B1 * | 5/2002 | Duhaylongsod | A61B 17/0281 600/228 |
| 6,599,240 B2 * | 7/2003 | Puchovsky | A61B 17/0206 600/201 |
| 6,808,493 B1 * | 10/2004 | Bookwalter | A61B 17/02 600/231 |
| 6,958,038 B2 * | 10/2005 | Feng | A61B 17/0293 600/228 |
| 2006/0290076 A1 | 12/2006 | Lees | |
| 2006/0293568 A1 | 12/2006 | Scjeodegger-Pluss | |
| 2007/0100212 A1 * | 5/2007 | Pimenta | A61B 5/0488 600/210 |
| 2008/0215081 A1 * | 9/2008 | Hsueh | A61B 17/0293 606/191 |
| 2009/0287062 A1 * | 11/2009 | Farley | A61B 19/26 600/231 |
| 2011/0270042 A1 * | 11/2011 | Giulianotti | A61B 17/02 600/228 |
| 2012/0022335 A1 * | 1/2012 | Assaker | A61B 17/0206 600/225 |
| 2013/0204091 A1 * | 8/2013 | Menendez | A61B 17/02 600/228 |

* cited by examiner

TELESCOPING SURGICAL SUPPORT AND RETRACTOR SYSTEM

CROSS-REFERENCE TO RELATED APPLICATIONS

This application claims priority to U.S. Provisional Application No. 61/487,593 filed May 18, 2011. The entire disclosure of the above-referenced application is incorporated herein by reference in its entirety.

TECHNICAL FIELD

The present disclosure relates generally to an adjustable system for supporting surgical tools.

BACKGROUND

Surgical tool support systems are used to securely and stably maintain surgical tools, such as surgical retractors, in a fixed position so that a physician or physician's assistant does not have to manually hold the tools throughout the duration of the surgical procedure. Some known surgical tool support systems include adjustable components which are removably mounted or otherwise attached to a surgical tool support or a horizontal bar, which is positioned over the patient and further connects in a fixed manner to the operating room table. An example of a surgical tool support is described in U.S. Pat. No. 4,143,652, the content of which is hereby incorporated herein by reference thereto.

Surgical tools that are commonly held by such surgical tool support systems include, for example, retractors for retracting internal organs, and other structures, such as a patient's ribcage. The Stieber Rib Grip Kit™ sold by Automated Medical Products Corp. is used, for instance, for retracting the ribs during abdominal surgery to retract the upper middle abdomen of a patient.

U.S. Pat. No. 6,302,843 describes a tool holder platform that can be mounted to horizontal bar that is positioned above a patient to hold a hydra, which, with various support arms, supports other tools such as a retractor to retract and maintain organs in the retracted position.

SUMMARY

The present disclosure relates generally to an adjustable system for supporting surgical tools. The surgical support system may include a primary telescoping support, secondary telescoping support supported from the primary telescoping support and configured for telescopically mounting a surgical tool thereto, such that telescoping of the primary support repositions the secondary telescoping support; and a positioning joint disposed between the primary and secondary telescoping supports for universally positioning and locking the secondary telescoping support with respecting to the primary telescoping support.

The positioning joint may have a plurality of articulations, preferably a first universally pivotable articulation connected to the primary telescopic support and a second articulation connected to the secondary telescoping support. The first articulation may be universally rotatable about an axis extending between the first articulation and an adjacent one of the plurality of articulations. The first articulation may also be universally rotatable about an axis extending between the first and second articulations. In one embodiment, both the first and second articulations are universally pivotable. For example, the positioning joint may include a first articulation connected to the primary telescopic support, and a second universally pivotable articulation connected to the secondary telescoping support.

In the preferred embodiment, the positioning joint may also include a linking articulation connected between the first and second articulations. The linking articulation could be, for example, a hinge pivotable about a single axis. In one embodiment, the axis of the hinge articulation may be fixed with respect to the first and second articulations. The first and second articulations may be universally pivotable and rotatable about the linking articulation. Preferably, the first and second articulations are ball-and-socket joints.

Preferably, the positioning joint further includes a lock control that is manually operable to lock the plurality of articulations in a single operation. Further, in some embodiments, the positioning joint may include a lock control that is manually operable to lock in position the first, second, and linking articulations in a single operation. In such embodiments, the positioning joint may also have rigid links connecting each adjacent articulation of the positioning joint. The lock control, in one embodiment, may also selectively lock and unlock the ball-and-sockets and the hinge in a single operation.

The surgical support system of claim 1, further comprising a base member comprising a rail clamp configured for securing the surgical support system selectively along surgical table guide rail.

Further, preferably, the secondary telescoping support has a ratchet to adjustably engage a rack of a retractor. Additionally, the primary telescoping support comprises a ratchet and a rack in telescoping association with respect to the ratchet, wherein the ratchet ratchets the rack to permit telescopic retraction of the rack and to prevent telescopic extension of the rack.

Further described herein is a surgical support in accordance with any of the above-described embodiments, and further including a positioning joint as is disclosed in U.S. Pat. No. 4,143,652, the content of which is herein incorporated by reference in its entirety. Specifically, disclosed is a surgical support system, which may include a primary telescoping support; a secondary telescoping support, the secondary support being configured for telescopically mounting a surgical tool thereto, such that such that telescoping of the secondary support with respect to the primary support repositions the secondary telescoping support; and a positioning joint disposed between the primary and secondary telescoping supports for universally positioning and locking the secondary telescoping support with respecting to the primary telescoping support.

While multiple embodiments are disclosed, still other embodiments of the present disclosure will become apparent to those skilled in the art from the following detailed description, which shows and describes illustrative embodiments. As will be realized, the invention is capable of modification in various aspects, all without departing from the spirit and scope of the present disclosure. Accordingly, the drawings and detailed descriptions are to be regarded as illustrated in nature, and not restrictive.

BRIEF DESCRIPTION OF THE FIGURES

While the specification concludes with claims particularly pointing out and distinctly claiming the subject matter that is regarded as forming the various embodiments of the present disclosure, it is believed that the embodiments will be better understood from the following description taken in conjunction with the accompanying Figures, in which:

DETAILED DESCRIPTION

While multiple embodiments are disclosed, still other embodiments of the present disclosure will become apparent to those skilled in the art from the following detailed description, which shows and describes illustrative embodiments. As will be realized, the invention is capable of modification in various aspects, all without departing from the spirit and scope of the present disclosure. Accordingly, the drawings and detailed descriptions are to be regarded as illustrated in nature, and not restrictive.

The present disclosure relates generally to an adjustable surgical support system and retractors that can be used therewith or independently. Referring to the one embodiment depicted in FIG. 1, an adjustable surgical retractor system 90 is shown mounted on an operating room table having a rail 101. A mounting member, such as a rail clamp or swinger clamp 102, is adjustably attached to the operating table rail 101. Suitable rail clamps 102 are described in U.S. Application Publication No. 2006/0290076, and U.S. Pat. Nos. 4,796,846 and 6,315,260, the contents of which are herein incorporated by reference in their entirety.

Figure 1:
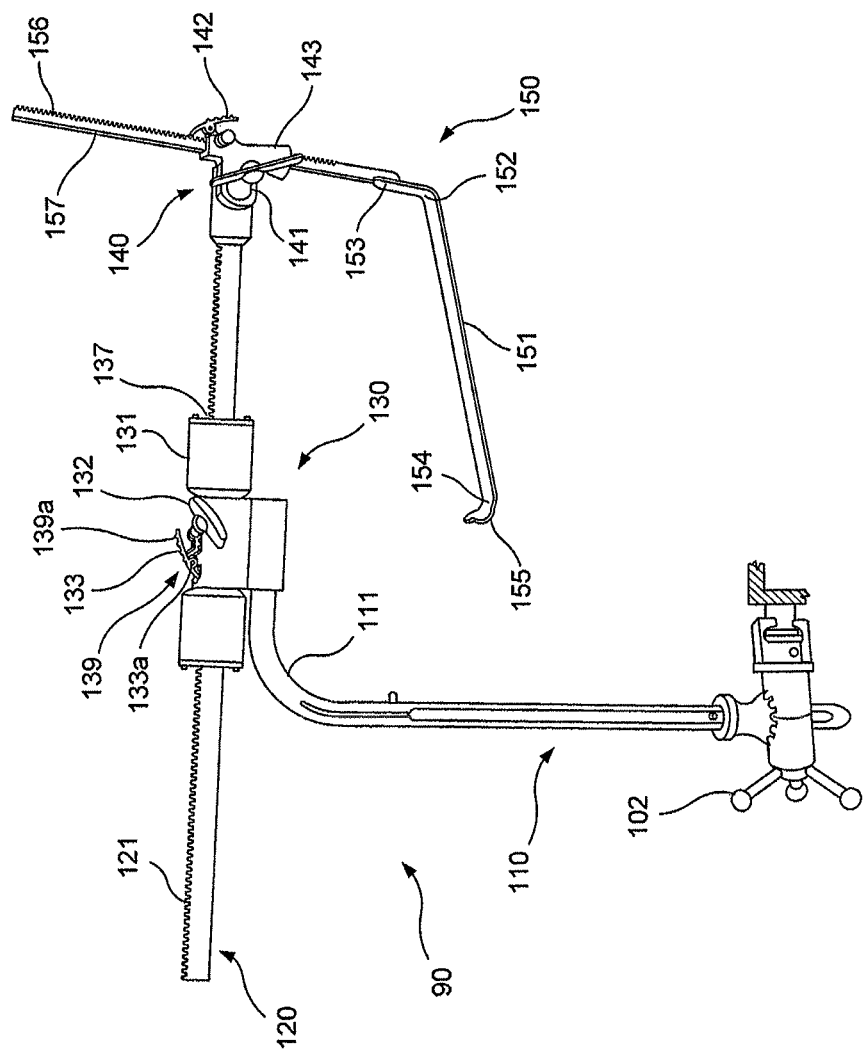
FIG. 1 depicts one embodiment of an adjustable surgical support system in accordance with the present disclosure.

A surgical tool support 110 is depicted adjustably positioned within the clamp 102. The surgical tool support 110, depicted in the embodiment of FIG. 1, is preferably of an L-shape, with a bend 111 transitioning fixedly at approximately 90° at the upper end of the support. Other suitable surgical tool supports, including adjustable surgical tool supports, are described in U.S. Application Publication 2006/0293568, the contents of which are herein incorporated by reference in their entirety. In a preferred embodiment, the length of the surgical tool support 110 may be 665 mm. In other embodiments, the length may be between 600 and 700 mm, or between 500 and 800 mm. Alternative supports can have other shapes, and can be straight or can include an attachment to a rail or another surgical support member.

At the top end of the surgical tool support 110 is depicted a first telescoping support component, which can be a horizontal support component 130 placed so as to extend over and across the patient on table 100. The preferred embodiment of the horizontal support component 130 includes a horizontal bar guide and a horizontal bar 120 to extend over the patient. The horizontal bar 120 includes a plurality of teeth 121, such as on the upper surface thereof. The horizontal bar 120 is inserted through the horizontal bar guide 131. The horizontal bar guide 131 includes an opening shaft 137 through which the horizontal bar 120 is received. Opening 137 can be a cylindrical bore or can have another shape, depending on the cross-sectional shape of bar 120.

Figure 4:
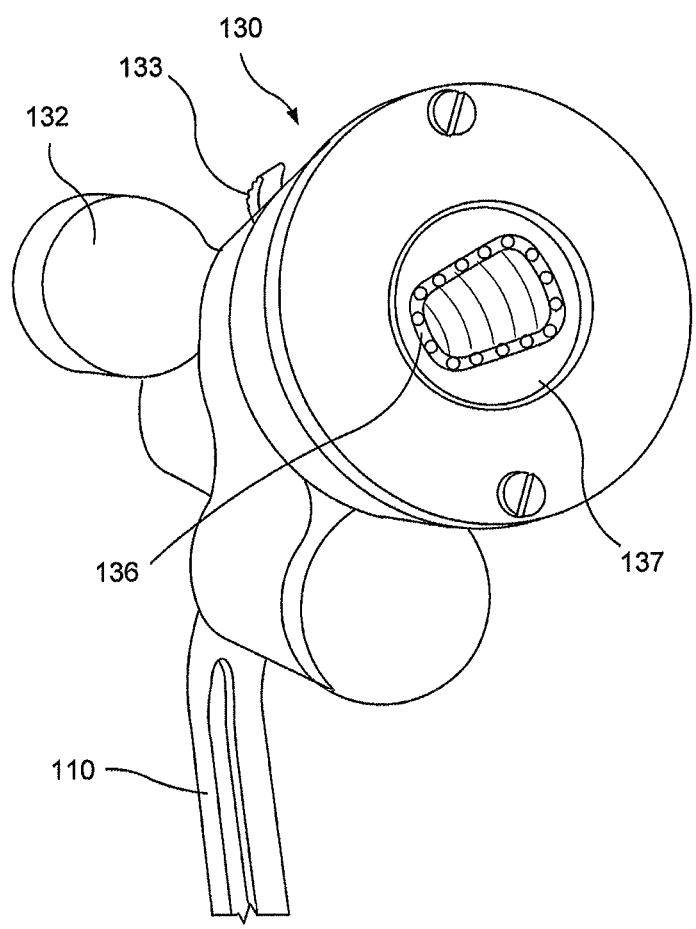
FIG. 4 depicts the interior of a horizontal bar guide component thereof.

As shown in FIG. 4, the interior of the opening 137 of the horizontal support component 130 can have bearings to facilitate sliding of the bar 120. Ball bearings are shown in elliptical races 136, although other types of bearings, including bushings can be used, and in one embodiment, a simple metal bore is provided.

The teeth 121 of the horizontal bar 120 cooperates with an adjustment component 132 of the horizontal bar guide. The adjustment component 132, in one embodiment, can include a pinion to engage the teeth 121 of the horizontal bar 121 to provide a rack and pinion to move, such as to telescope, the bar 120 for adjusting the position of the horizontal bar 120 horizontally. A manipuable portion 132 of the horizontal support component 130 is disposed and configured to be exterior of the horizontal bar guide 131, connected with the pinion which extends into the interior of the bar guide 131 to operate the rack and pinion. Alternative embodiments can have other mechanisms to move, position, and/or lock the bar 120 with respect to the support 110, such as with a pure ratchet or other arrangements.

Figure 3:
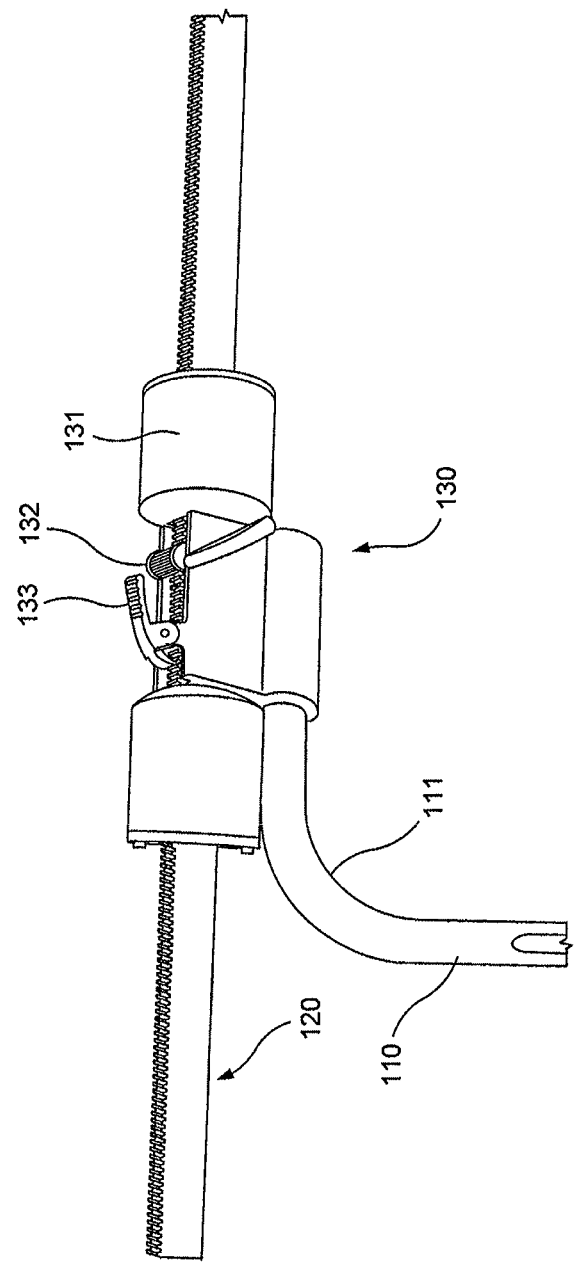
FIG. 3 depicts an example horizontal support component of the surgical support system shown in FIG. 1.

FIG. 3 depicts a close-up view of the horizontal support component 130 of the embodiment of FIG. 1. The teeth 121 of the horizontal bar 120 are showing greater detail, as is the cylindrical shape of the horizontal bar guide 131. The ratchet 133 is also visible with the teeth contact and being within the support component 130, and the finger pad 139a being exterior. The adjustment component 132, the interior portion of which in this embodiment is a pinion for cooperation with the rack (teeth 121) of the horizontal bar 120, is also shown on the horizontal support component 130.

Further included on the horizontal support component 130 is a ratchet 139 mechanism. The preferred ratchet includes a pivoting jaw 133 that is spring-loaded or otherwise biased into ratcheting engagement with the teeth 121 of the horizontal bar 120. The contact point between the jaw 133 and the teeth 121 may be in the form of a pawl. The teeth 121 and the ratchet jaw 133 cooperate in such a manner that when the ratchet is in contact with the teeth, the horizontal bar 120 can only be moved in one direction, preferably distally with respect to the incision, towards the upright support 110. Movement in the other direction, proximally with respect to the incision, is prevented by the ratchet when it is engaged. In this manner, tension provided by tissue that is being held by a retractor on the far end of the bar 120 is resisted, but adjustment of the bar in the other direction is quick and easy without disengaging the ratchet. To move the horizontal bar 120 in the distal direction (proximally, away from the rail clamp), the ratchet is lifted by a user out of engagement with the teeth 121, such as by depressing on a finger pad 139a on an opposite side of the ratchet pivot 133a from the jaw 133, thereby allowing the horizontal bar 120 to be moved in either direction. The rack and pinion, or other incremental adjustment mechanism to move the bar 120, is preferably configured to allow the bar 120 to be moved by directly pulling on the bar distally, towards the rail clamp. In a preferred embodiment the length of the horizontal bar 120 may be 440 mm. In other embodiments, the length of the horizontal bar 120 may be between 400 mm and 480 mm, or between 350 mm and 550 mm.

At one end of the horizontal bar 120 is a secondary adjustment member 140. In some embodiments, the secondary adjustment member 140 may include mechanisms similar to the horizontal support component 130. The secondary adjustment member 140 may include an opening therethrough for accepting an mounting portion 157 of a surgical retractor 150. The mounting portion 157 of the surgical retractor 150 may have teeth 156 on an outward surface thereof similar to teeth 121. An adjustment component 141 of the secondary adjustment member 140 may be configured similar to the adjustment component 132 of the horizontal support component 130. Some embodiments can include, for example, a rack and pinion and/or a ratchet relationship between the adjustment component 141 and the teeth 156, or any other known adjustable relationship or configuration. The preferred embodiment is shown with a ratchet 142 of the secondary adjustment member 140 may cooperate with the teeth 156 of the mounting portion 157 of the retractor 150 a similar manner as with the ratchet 133 and the horizontal bar 120. The secondary adjustment member may also be rotatably adjustable in the plane of the horizontal bar about its connection point to the horizontal bar 120. The degree of rotatable adjustability may be between +/−20°, +/−40°, or +/−70° from vertical. The length of the mounting portion 157 of the retractor 150 may preferably be 150, 170, or 200 mm. In some embodiments, the length may be between 130 and 220 mm, or it may be between 100 and 250 mm.

In preferred embodiments, an insertion end 143 of the secondary adjustment member is flared so as to easily receive the mounting portion 157 of the retractor 150. While the axial cross-section of the opening of the secondary adjustment member is preferably shaped to prevent or limit axial rotation of the retractor, the flared end can flare from that shape to another to easily receive the tip of the mounting portion 157. For instance, in the embodiment shown, the mounting portion 157 cross-section is generally square, as is the cross-section of the mounting portion 157, and the flared guide end becomes generally rounded or circular with a substantially larger cross section, e.g. about 2 to 10 times as large as the cross section holding the adjustment member from rotations. During surgery, a surgical team will position the retractor within the patient, and then may easily position and adjust the surgical retractor system so that the insertion end 143 of the vertical support component is placed over the mounting portion 157 to receive and secure the retractor 150.

Figure 5:
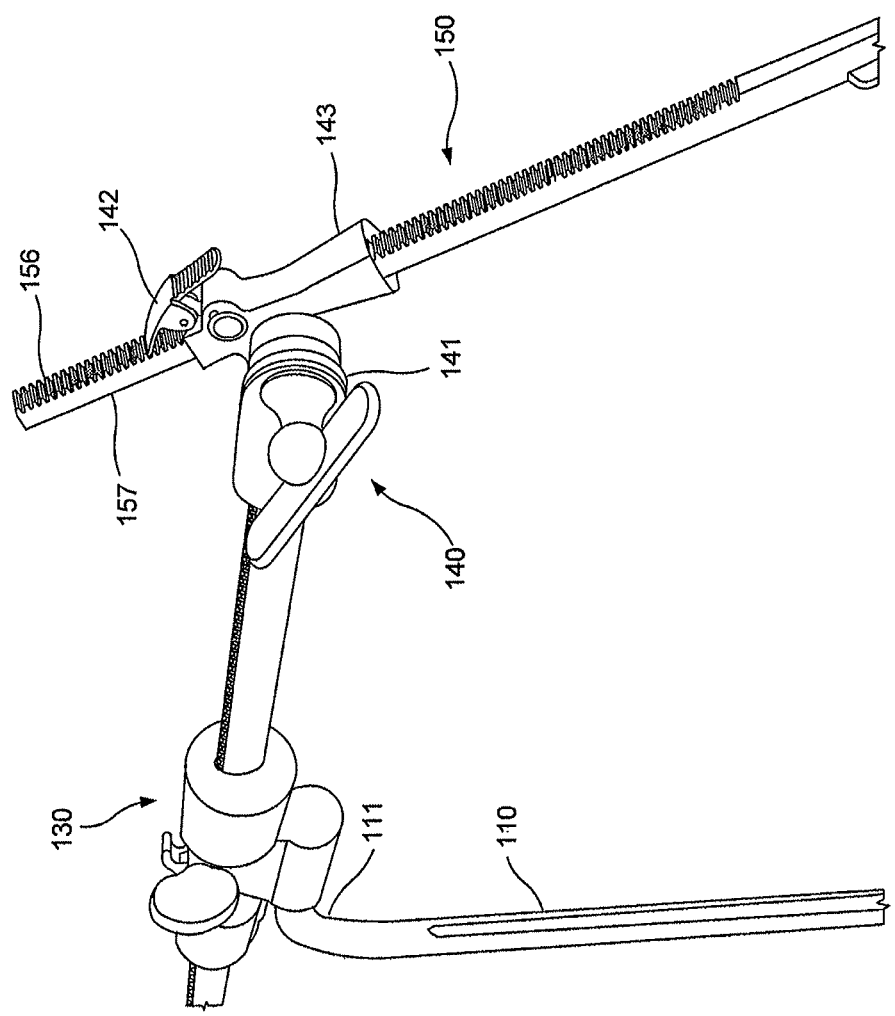
FIG. 5 depicts an example surgical retractor support component the surgical support system shown in FIG. 1.

FIG. 5 depicts a close-up view of the secondary adjustment member 140 and the mounting portion 157 of the retractor 150. The flared insertion end 143 of the secondary adjustment member 140 is more clearly visible, the retractor, and the teeth 156 thereof, inserted therethrough. The teeth contacting end of the ratchet 142 (e.g., a pawl) is shown contacting the teeth 156, thereby allowing the retractor to be adjusted upwardly, but not downwardly. To adjust the retractor 150 downwardly, the depression end of the ratchet 142 would be pressed so as to remove contact between the ratchet and the retractor.

Figure 7:
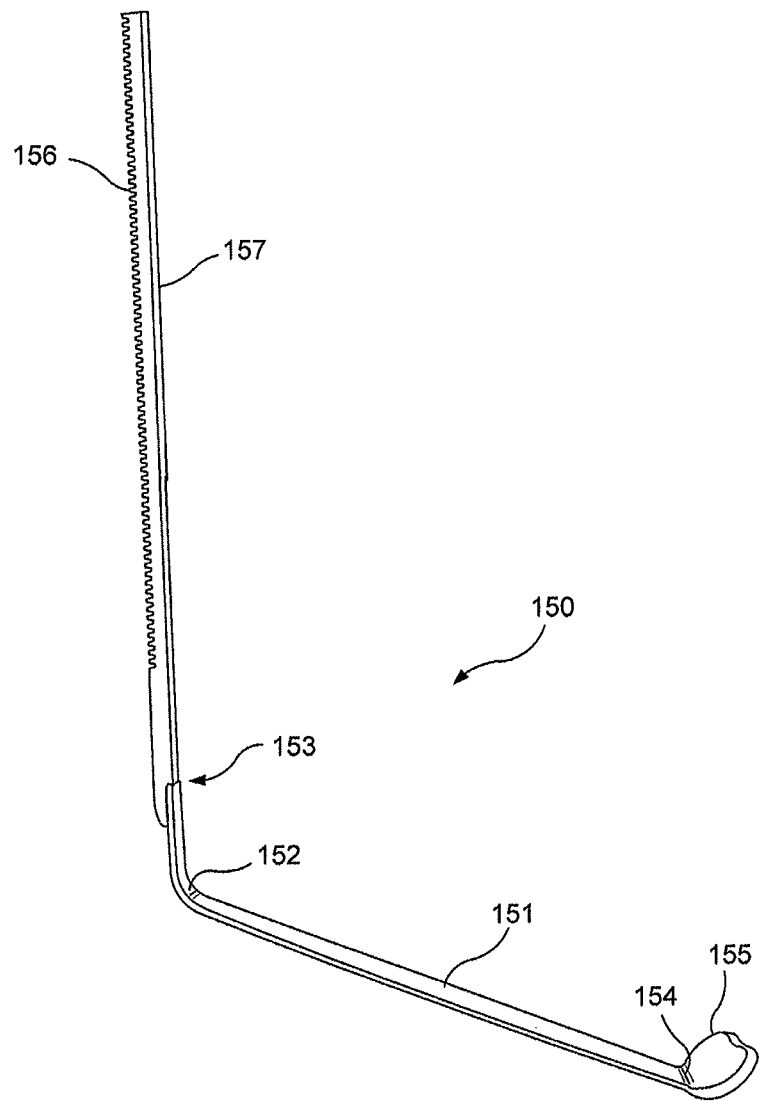
FIG. 7 depicts an example surgical retractor suitable for use with an adjustable surgical support system in accordance with the present disclosure.
Figure 8:
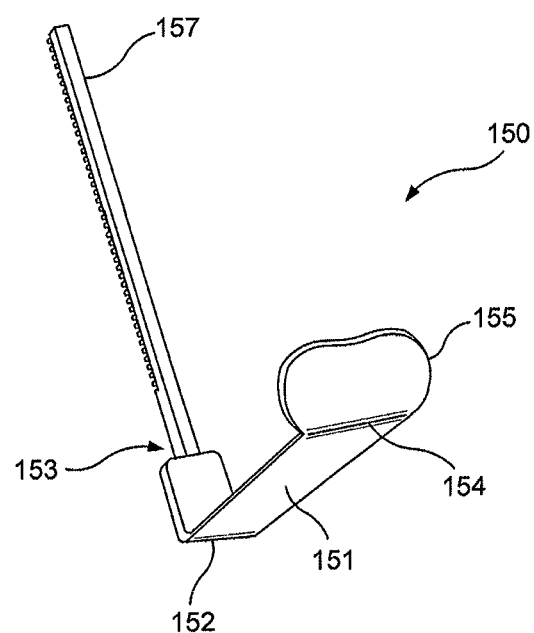
FIG. 8 depicts another of the surgical retractor shown in FIG. 7.

The surgical retractor 150 may include a mounting portion 157, as discussed above, which can be welded (at 153) or otherwise affixed or secured to a retraction portion, such as a retractor blade 151, which preferably has a flat and straight base. In one embodiment, the angle between the mounting portion 157 and the blade 151, about bend 152, is approximately 110°. Other angles are possible, as will be discussed in greater detail below, including 90°, or between about 70° or 80° and 130° or 140°, or a range between 70° and 130°. A lip 155 is positioned on the end of the retraction portion 151 opposite the bend 152. A 155 is preferably provided at the distal tip of the blade 151 that is inserted within the patient and serves to help retract and retain retracted the desired anatomy for surgery. In some embodiments, the lip 155 may be generally heart-shaped, and bent inwardly at an angle (at 154) to the retraction portion 151, or can have other shapes. The preferred lip is preferably bent as an angle upwards from the blade base, towards the side of the mounting portion 157, thereby allowing the horizontal bar 120 to be moved in either direction. Further, FIG. 7 depicts a close-up of a retractor 150 in accordance with the embodiment of FIG. 1. Additionally, FIG. 8 depicts a close-up view, at a different angle, of a retractor 150 in accordance with the embodiment of FIG. 1.

Figures 9A, 9B, 9C:
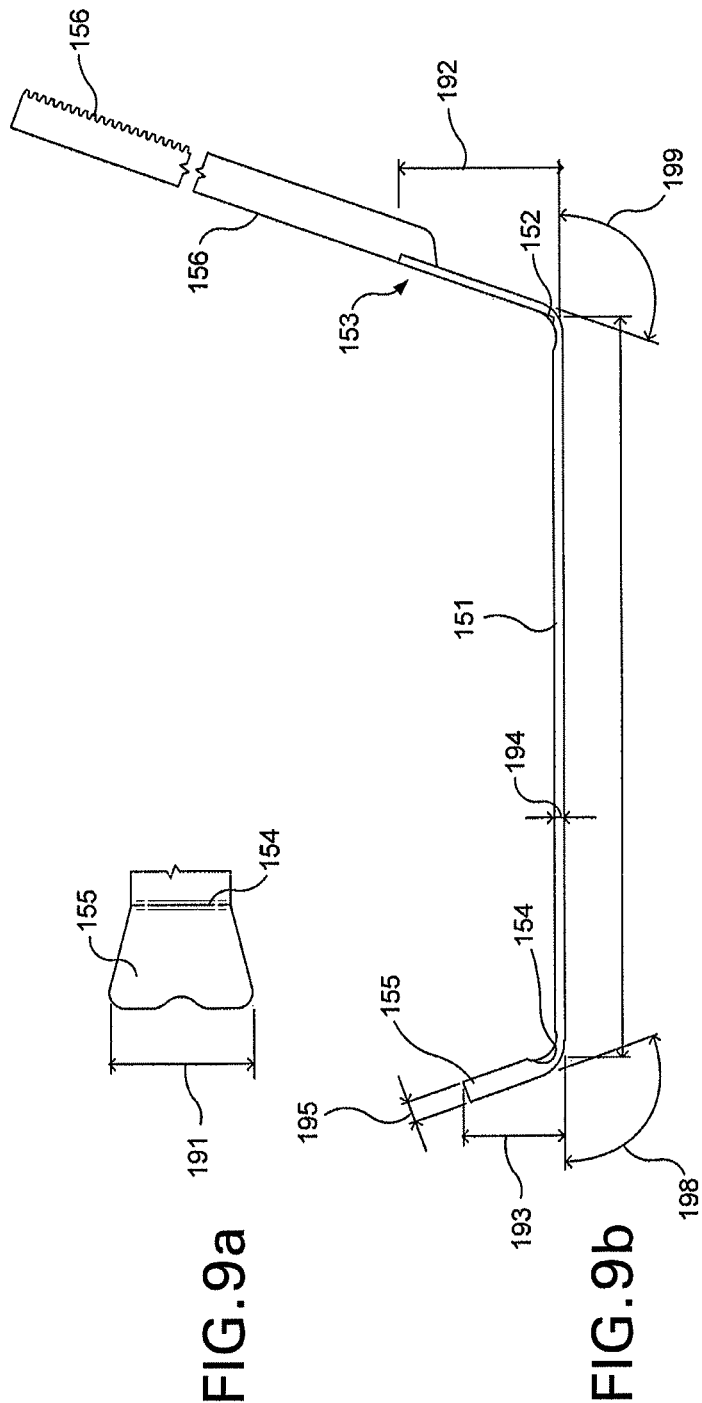
FIGS. 9a-c are diagrams of the surgical retractor shown in FIG. 1.
Figure 10:
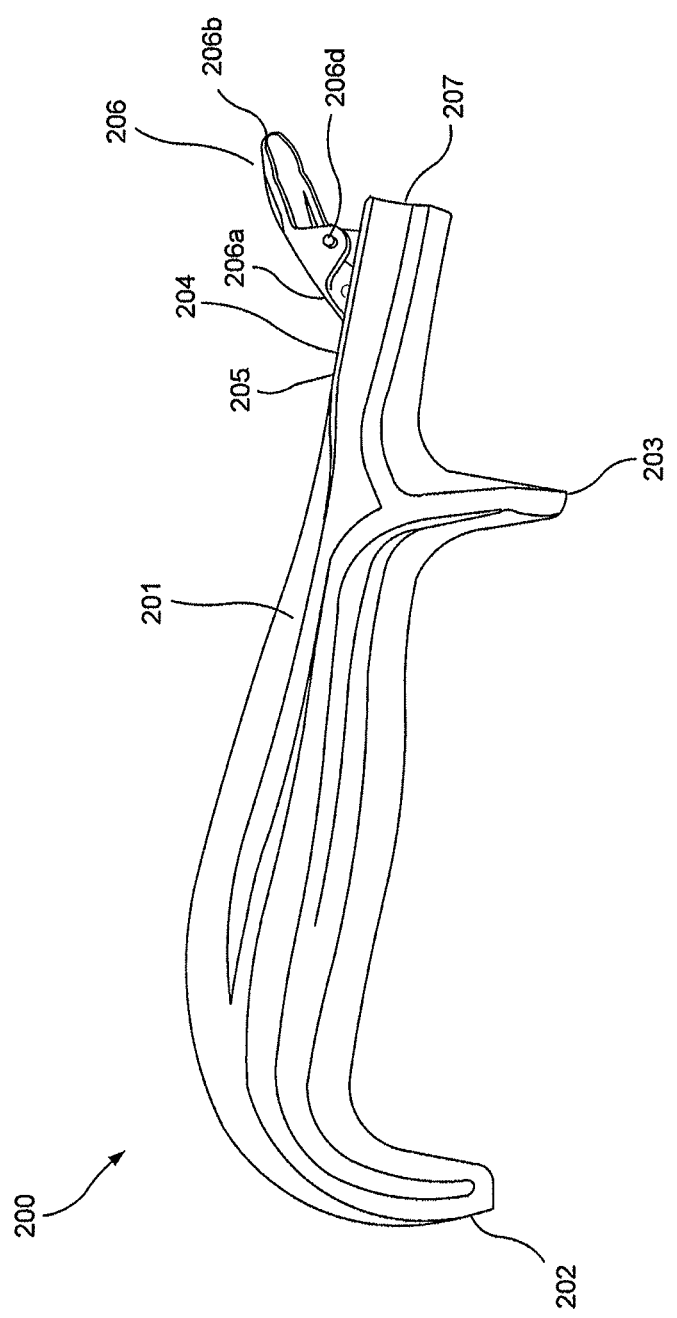
FIG. 10 depicts an embodiment of a retractor handle suitable for use with the adjustable surgical support system in accordance with the present disclosure.

FIG. 9 depicts a schematic illustration of a retractor 150 in accordance with adjustable retractor system of some embodiments of the present disclosure. In particular, lip 155 may be heart-shaped and width 191 preferably of about 30 mm, or about 25 mm-35 mm, or about 20 mm-40 mm. In other embodiments, it may be between 20 and 50 mm in width or other desired sizes. The distance 192 between weld 153 and bend 152 is preferably about 30 mm in one embodiment. In other embodiments, it may be between 2 and 100 mm, for example, although other distances can be used. Several retractors can be provided in a kit, having lengths of the retraction portion 151 such as 150, 170, or 200 mm. In some embodiments, the length may be between 100 and 250 mm, for example. The angle 198 of bend 154 may preferably be 110°, or it may be between 100° and 120°, or 80° and 140°. Other angles can be selected. The bend 152 may be formed of a very small, sharp radius, e.g. 3, 4, 5, 6, or 7 mm, and the angle 199 thereof may be between about 80° and about 140°, or preferably between about 100° and 120°. The portions of the retractor which connect to and terminate at the bend 152, the blade 151 and the mounting portion 157, are substantially straight. The height 193 of the lip 155 may be about 20 mm in a preferred embodiment although other heights, such as between 10 and 30 mm can be used in other embodiments. The thickness of blade 151 and lip 155 (thicknesses 194, 195, respectively) may be 3 or 4 mm in preferred embodiments, and is typically between about 1 mm and 5 mm in other embodiments. The thickness 194 of the blade 151 can be the same or different than the thickness 195 of the lip 155 or other parts of the retractor. The width 196 of the retraction portion 151 maybe 20 mm in a preferred embodiment. In alternative embodiments it can be between about 10 mm and 30 mm, for example, although other widths can be selected. The width 197 of the lip may be slightly larger than that of the retraction portion at its widest part, for example, preferably 25 mm, or more generally between about 10 mm and 50 mm.

Figure 2:
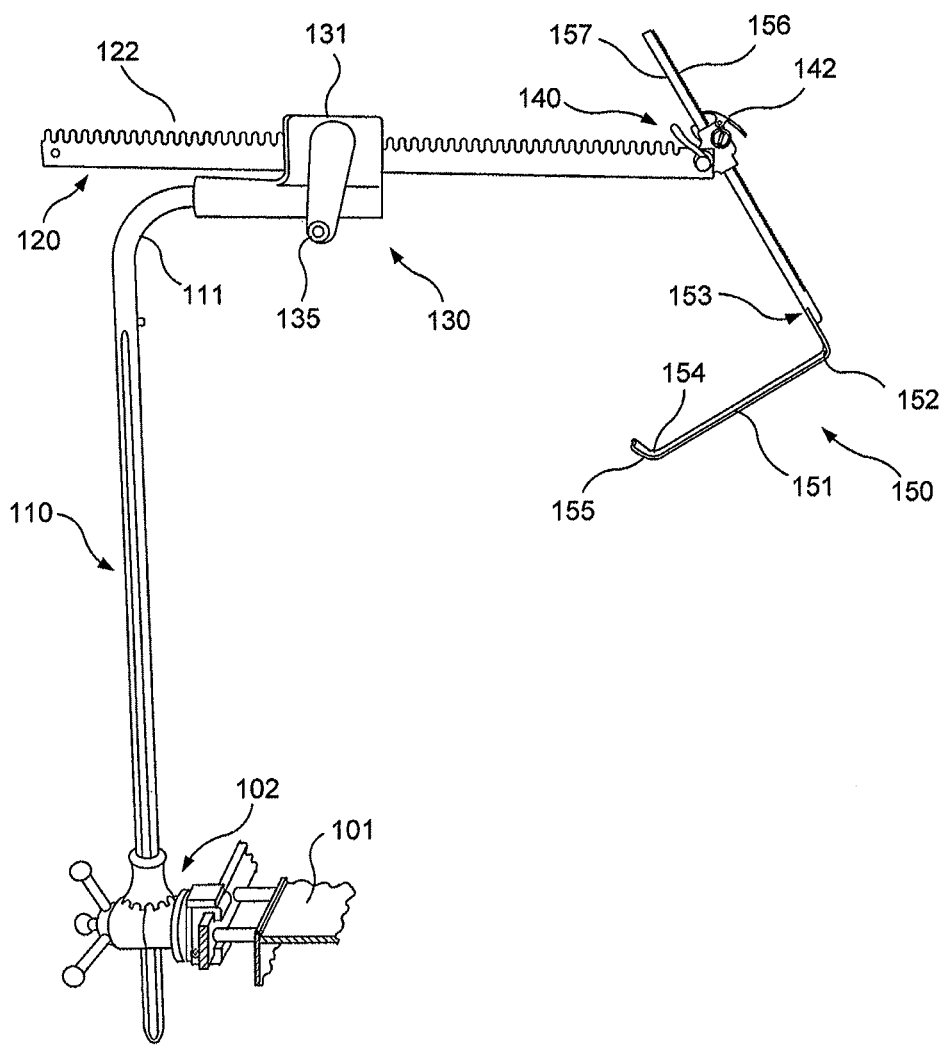
FIG. 2 depicts another embodiment of an adjustable surgical support system in accordance with the present disclosure.

Depicted in FIG. 2 is another example embodiment of an adjustable surgical retractor. In this embodiment, the horizontal bar 120 is configured with notches 122 as opposed to the teeth 121 depicted in FIG. 1. These notches 122 cooperate with an adjustment handle 135 of the horizontal support component 130, so rotation of the handle causes horizontal movements of the horizontal bar 120 in either direction, depending on which direction the handle 135 is rotated. An internal component of the handle 135 contacts the notches 122 and causes them to be pushed horizontally in either direction when the exterior portion of the handle 135 is rotated. This embodiment provides an alternative rack and pinion arrangement, in which the pinion has over-center positions within the rack so that no ratchet is needed to resist or prevent movement of the rack in either direction without rotating the handle. Further, it is noted that in this depicted embodiment, the bend 152 of the retractor 150 is approximately 90°, as opposed to the approximately 110° of FIG. 1.

Figure 6:
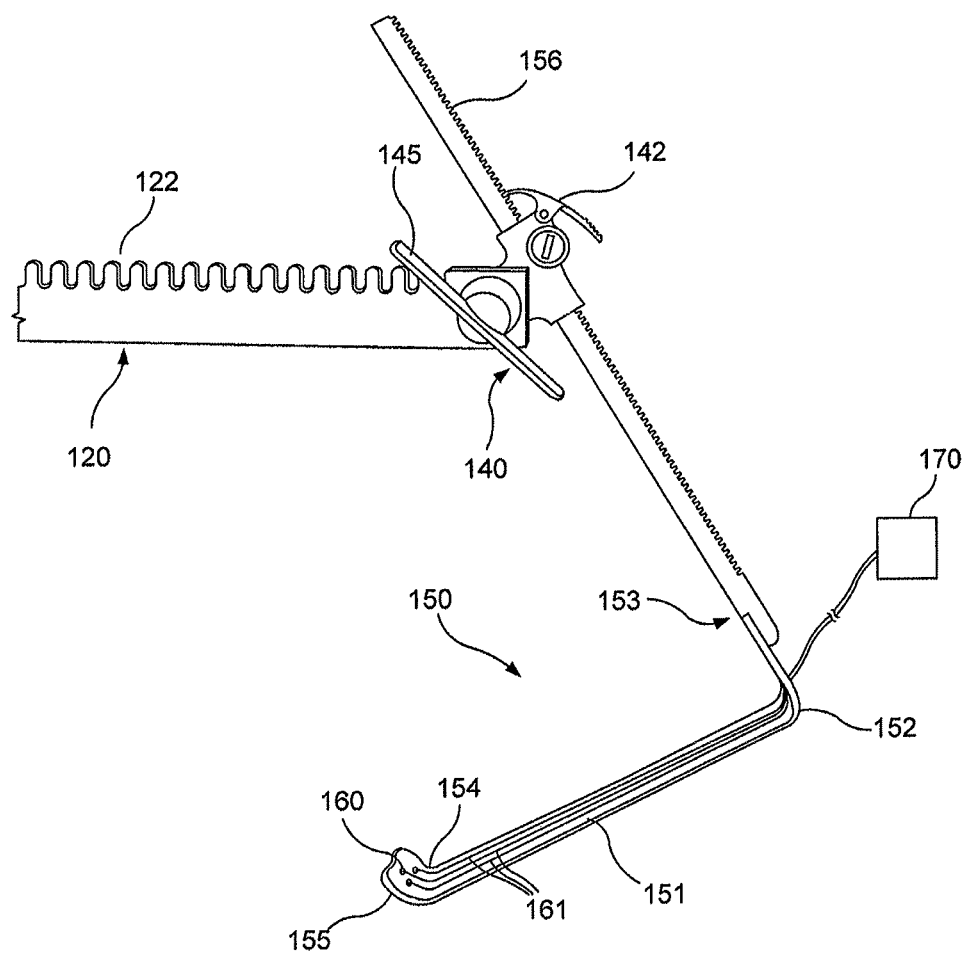
FIG. 6 depicts an example surgical retractor support component the surgical support system shown in FIG. 2.

FIG. 6 depicts a close-up view of a retractor 150 in accordance with the embodiment of FIG. 2. On the upper surface of the retraction portion 151 of the retractor 150 are three wires, tubes, or other connections 161 associated with three surgical instruments or sensors, such as suction, a light or other fiber optics, and a sensor such as to interact with a cell of the thyroid or another cell to detect cancer or another condition. The instruments and/or sensors and/or their connections 161 may be inserted through holes 160 of the lip 155 of the retractor 150 or another part of the blade. The cables are connected to instrument bases 170, at another location within the surgical environment.

Referring now generally to FIGS. 10-13, a retractor handle 200 suitable for use with the presently disclosed surgical retractor system is depicted. The handle 200 may generally include an axial portion 201 being formed of a generally cylindrically-shaped piece of stainless steel, having irregular diameter across its length so as to conform to the grip of a human hand. On both the proximal and distal ends of the axial portion are located lateral extensions 202, 203. Lateral extensions 202, 203 extend laterally from the axial portion. Extensions 202, 203 are spaced apart from one another between about 3 inches-6 inches, or preferably 4 inches-5 inches, to conform to the width of a human hand while the hand is gripping the axial portion 201. Extensions 202, 203 may generally extend between about 0.5 inches-3 inches, or more preferably between about 1 inch-2 inches. A distal extension 204 extends distally from the distal end of the axial portion 201 and generally forms a hollow square of proportions to meet with the mounting portion 157 of a surgical retractor 150. The distal extension 204 generally extends from the axial portion 201 between about 1 inch-4 inches, or preferably between about 1.5 inches-3 inches.

Mounted on an outward surface 205 of the distal extension 204 is a ratchet 206. The ratchet 206 is configured and operates in a manner similar to ratchet 142 of the secondary adjustment member, as described above, having a biasing spring 206c and a pivot point 206d. The ratchet 206, via a teeth contacting end 206a thereof (which may be in the form of a pawl, as discussed above), cooperates with the teeth 156 of the mounting portion 157 of a retractor 150 through an opening 209 on the outward surface 205 of the distal extension 204 (see FIGS. 12 and 13), such that, when the mounting portion is inserted into an open end 207 of the distal extension 204, the retractor 150 by its mounting portion 157 is locked in cooperative association with the handle 200. To release the retractor 150 from the handle 200, a finger pad 206b of the retractor 206 is depressed, thereby releasing contact between the contacting end 206 and the teeth 156, allow the mounting potion 157 to slide-out from within the distal extension 204.

In use, a surgeon or other operator may generally insert the mounting portion 157 of the retractor 150 within the distal extension 204 of the handle 200 to cooperatively lock the two components together. (See FIGS. 12 and 13). The surgeon then grips the axial portion 201 of the handle 200 and manipulates the retractor 150 into position within the patient, i.e. retracting a particular anatomy. Once in the desire position, the handle 200 is released from the retractor by depressing the finger pad 206b, releasing the cooperative association between the mounting portion 157 (and the teeth 156 thereof) and the contacting end 206a of the ratchet 206, allowing the mounting end 157 to slide-out of the distal extension 204 of the handle 200.

Figure 11:
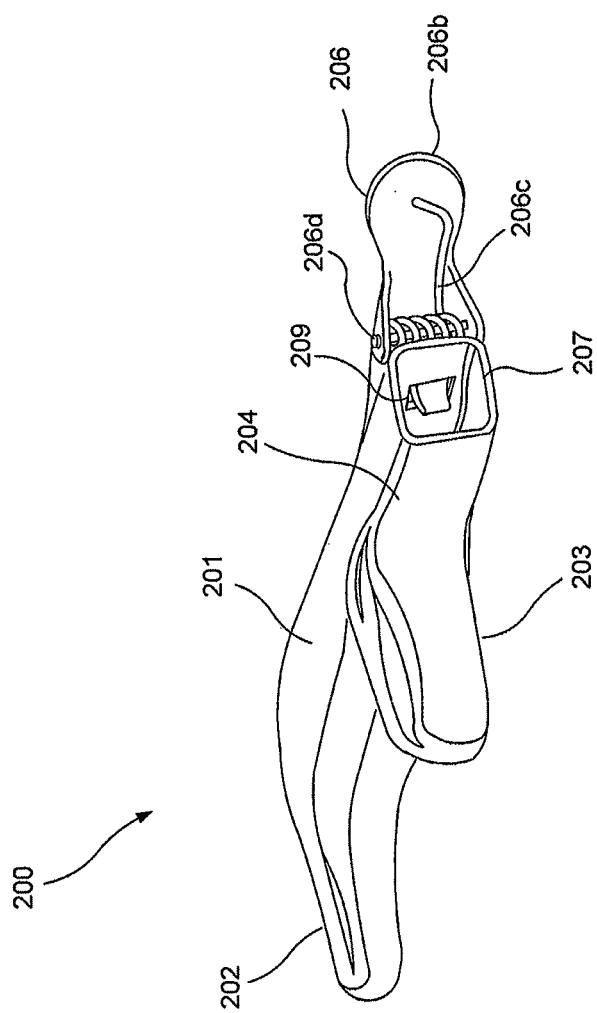
FIG. 11 depicts an axial view of the retractor handle shown in FIG. 10.

FIG. 11 depicts an axial view of the handle 200, looking into the open end 207 of the distal extension 204. The spring 206c is positioned on the underside of the ratchet 206 and is configured to bias the ratchet about its pivot point 206d in a position to contact teeth 156 when the mounting portion 157 is present.

Figure 12:
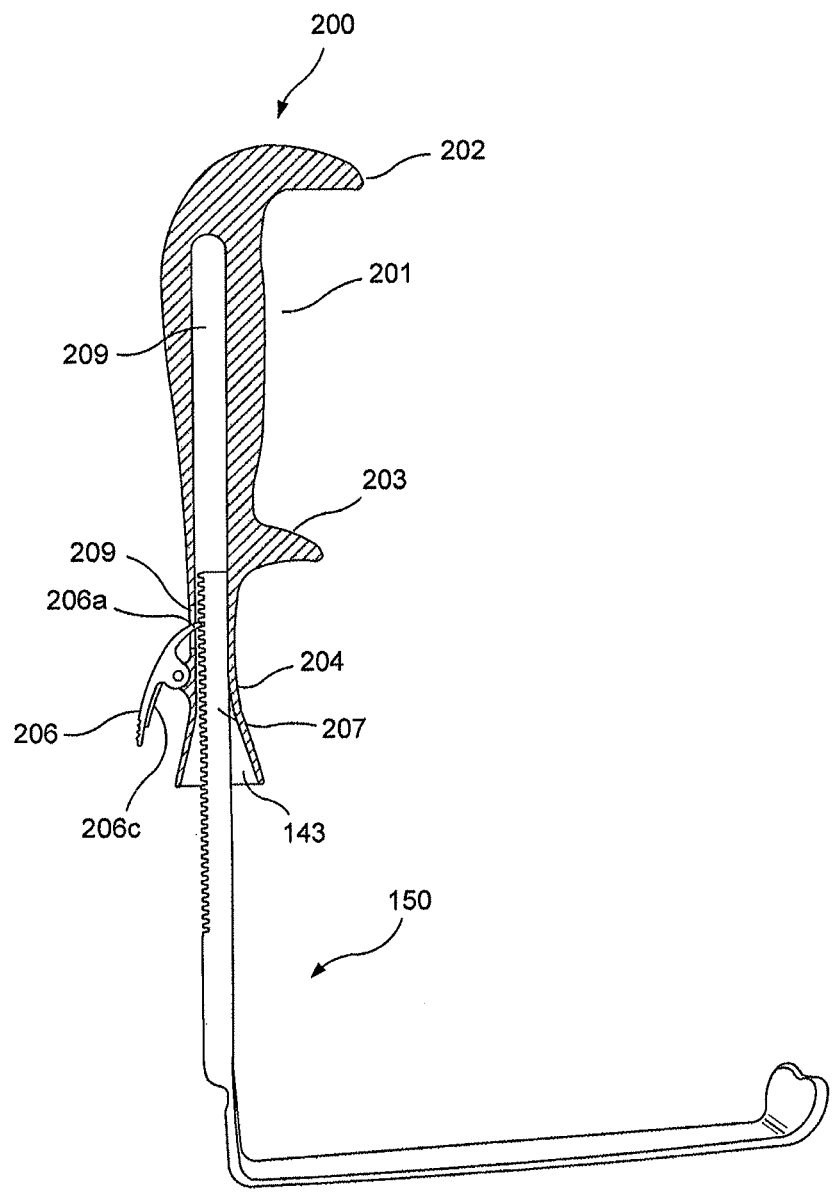
FIG. 12 depicts a retractor handle connected to a retractor in a cross-section view.

FIG. 12 depicts a cross-section view of a handle 200. As shown, the inside channel 209 through which the mounting portion of a retractor 150 may be inserted extends substantially the entire length of the axial portion 201. In this embodiment, the handle 200 further includes a flare 143 at distal extension 204. The flare 143 allows easier insertion of the mounting portion of the retractor 150 into the handle 200 As also shown in FIG. 12, the pawl of the ratchet 206 is contacting teeth of the mounting portion, thereby securely holding it in place at the desired length.

Figure 13:
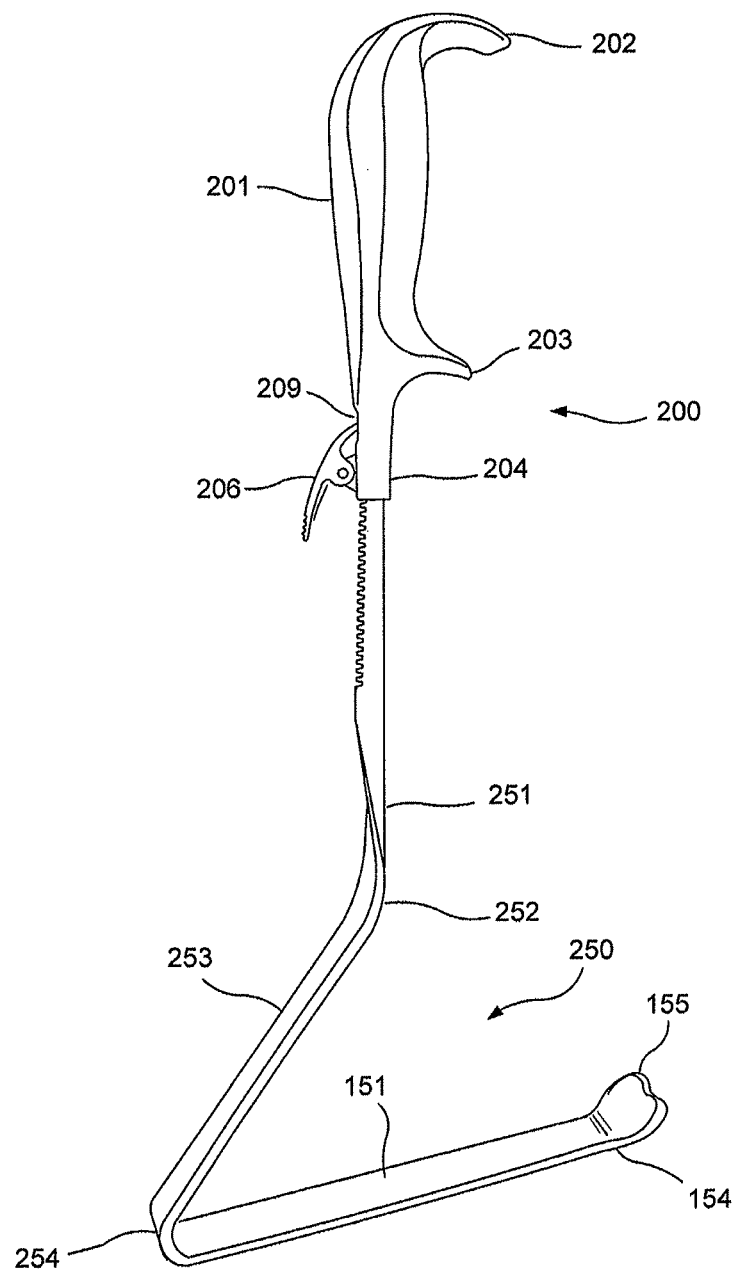
FIG. 13 depicts an example retractor having an angled side.

FIG. 13 shows an additional embodiment of a retractor 250 connected to a handle 200. The retractor 250 had a configuration especially suited for use with robotically-performed surgery, wherein the retractor 250 is configured to avoid contact with robotic arms during such surgery. The retractor 250 includes a connection portion 251, which may be, for example, welded to, and extending from a mounting portion (as described above, e.g., mounting portion 157). A first bend 252 is angled below the connection portion at a generally obtuse angle, for example, about 170, 160, 150, 140, 130, 120, 110, or 100 degrees from the mounting portion. The first bend 252 is positioned between the connection portion 251 and a side 253, which extend from the bend 252 at the desired angle. Side 253 is connected to blade 151 with a second bend 254. The second bend 254 may generally form an acute angle, for example, about 20, 30, 40, 50, 60, 70, or 80 degrees. As described above, in a preferred embodiment, blade 151 may have a heart-shaped lip 155. Alternatively, lip 155 may be a generally rounded shape. The first and second bends 252, 254 allow the side 253 to remain clear of a robotic arm during surgery, while still allowing the blade 151 to be properly positioned. The retractors described in the present disclosure are sufficiently strong to retract a shoulder for providing space for surgical entry through the axilla.

The surgical support, retractors, and handle of the present disclosure may be used in performing various surgeries, including thyroid surgery wherein the thyroid is accessed through the axilla, as well as vaginal and rectal surgeries, and as examples other surgical procedures in which a surgical tool is supported or for example a deep incision or body opening is to be retracted. In one embodiment, a surgeon or surgical technician may position the retractor 150 in the desired location and orientation, sometimes cutting against the bottom side of the retractor blade 151 as the blade 151 is inserted into the incision. The height and angle at which the upright surgical tool support 110 is connected to the rail 101 of the operating table 100 is then adjusted, including by positioning and manipulating the swinger clamp 102 and tightening it onto the rail 101 and upright support 110. Then, the horizontal bar 120 is adjusted horizontally within the horizontal support component 130 and over the patient, in the manner described above rotating the manipuable 132, or by simply pulling on the bar 120, which may or may not require depressing the ratchet 133 (depending on which direction the bar is moved, as discussed above). The flared insertion end 143 of the vertical support component may then be guided over the adjustment portion 157 of the retractor 150, and secured in position at the appropriate point along the adjustment portion 157. If the retractor needs to be repositioned once guided within the vertical support component 140, the adjustment portion 141 and/or the ratchet 142 may be manipulated as necessary, in the same manner as the like components of the horizontal support component 130.

Figure 14:
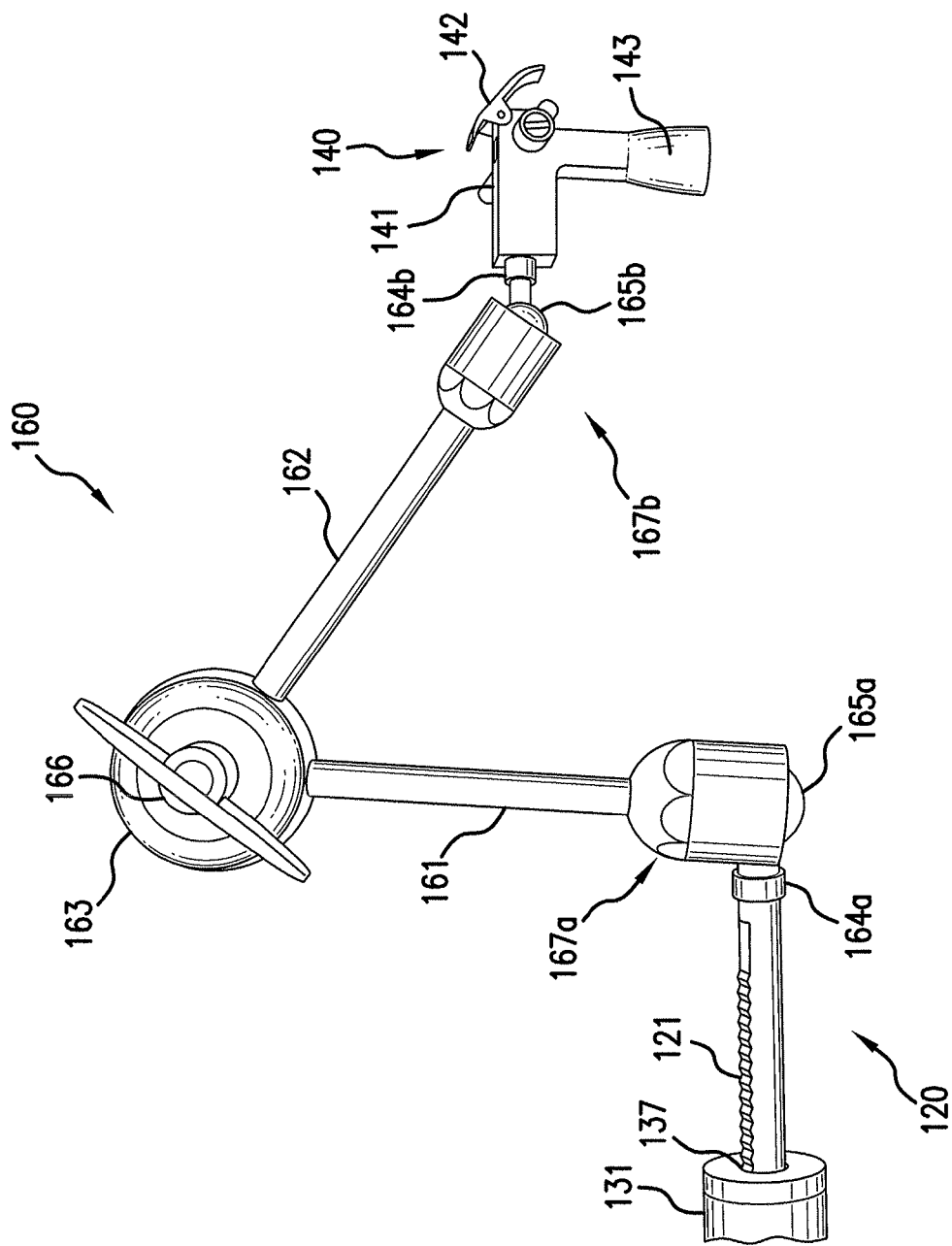
FIGS. 14-17 depict an embodiment of an adjustable surgical support system in accordance with the present disclosure that includes a positioning joint.
Figure 15:
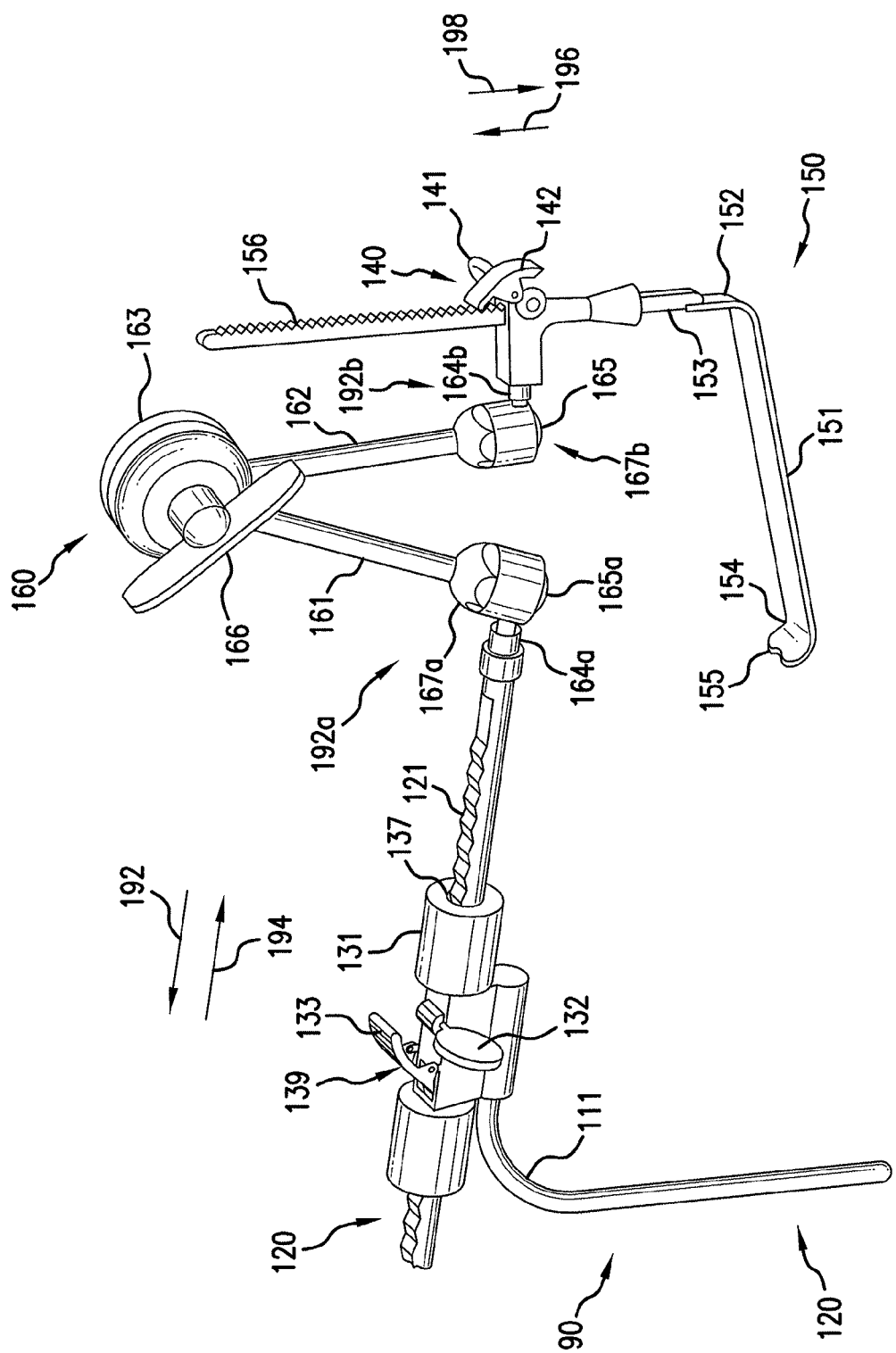
Figure 16:
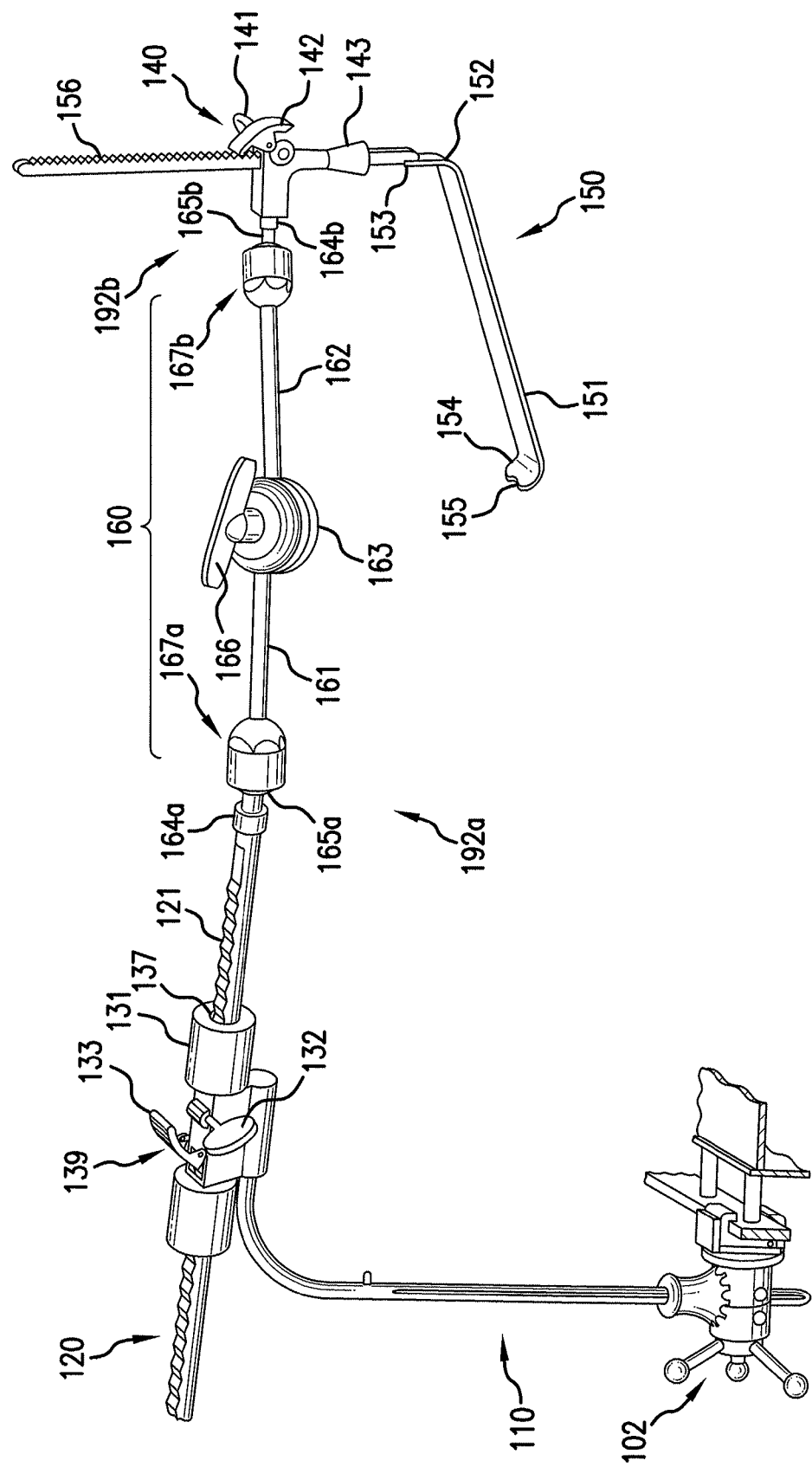

A further embodiment is disclosed with reference to FIGS. 14-16. This embodiment can include any of the features of any of embodiments described above, and can further include some or all of a positioning joint 160. In one embodiment, the system comprises a surgical support system, which may include a primary telescoping support; a secondary telescoping support, the secondary support supported from the primary telescoping support and being configured for telescopically mounting a surgical tool thereto, such that such that telescoping of the primary support repositions the secondary telescoping support; and a positioning joint disposed between the primary and secondary telescoping supports for universally positioning and locking the secondary telescoping support with respecting to the primary telescoping support.

As discussed in the earlier figures, the primary telescoping support comprises a rachet and a rack in telescoping association with respect to the ratchet, wherein the ratchet ratchets the rack to permit telescopic retraction of the rack and to prevent telescopic extension of the rack. As shown in FIG. 15, the primary telescopic support, in this example 120, may be moved in a proximal direction 194, or in a distal direction 192. The secondary telescopic support also has a ratchet to adjustably engage a rack of a retractor. As shown in FIG. 16, the secondary telescopic support, in this example 150, may be retracted in an upward direction 196, or extended in a downward direction 198.

The positioning joint can have one or more legs, for example, one, two, three or more legs, and preferably has two legs. The system can have one or more articulations, at least one of which that is universal to allow universal positioning. In the embodiment shown, the joint 160 has two universal articulations 192*a*, 192*b*, one at each end of the universal joint 160, and a linking articulation 163 between the two universal articulations 192*a*, 192*b*. The universal articulations 192*a*, 192*b* can be universal pivotable or rotatable. Preferably, the first and second universal articulations being pivotable with respect to the first and second telescopic support, respectively, and rotateable about the axis connecting the two articulations 192*a*, 192*b*.

The positioning joint 160 may be lockable to securely position the articulations. The positioning joint 160, preferably, can simultaneously lock ends thereof, where, for example, the telescopic supports may be adjustably adjoined. The positioning joint 160 may be lockable to securely position such components. Preferably, the universal articulations 192*a*, 192*b* are ball and socket connectors at the ends of the legs to accomplish this secure positioning as shown in FIGS. 14-16. The ball and socket connectors may be universally positional in three dimensions, or may be partially positionable in two or one dimensions.

With reference now to a preferred embodiment of a positioning joint, e.g., as is generally disclosed in U.S. Pat. No. 4,143,652, the joint 160 can include one, two, three, or more rigid links or rods, e.g. rods 161, 162, operatively adjacent or connected in series to one another by a plurality of articulations, such as a pin joint or hinge or other suitable component. These articulations may be universally pivotable about its axis. In the preferred embodiment, the rods are straight; however, in alternative embodiments, the rods may be curved or of varying shapes and sizes.

As discussed above, in the preferred embodiment, a ball-and-socket joint embodying a ball 165*a,b* and a bolt or pin 164*a,b* formed thereat is provided at either end of the positioning joint 160. The sockets are shown as elements 167*a,b*. Preferably, all three joints or hinges of the positioning joint 160, i.e. both of the ball-and-socket joints 164*a,b*, 165*a,b* as well as the linking articulation 163, provided between the rods 161, 162 can be arrested in position and released by a single adjustment component, which can include a turnkey, a handwheel, a clamping lever, or equivalent, etc. In the preferred embodiment, the linking articulation is a pin joint or hinge pivotable about a single axis and the hinge articulation is fixed with respect to the first and second articulations; however, the linking articulation may be universally pivotable about its axis or may be a ball-and-socket or any similar moveable joint. Thus, the positioning joint 160 is preferably universally positionable to position and secure horizontal bar 120 and adjustment member 140 at ends thereof.

Figure 17:
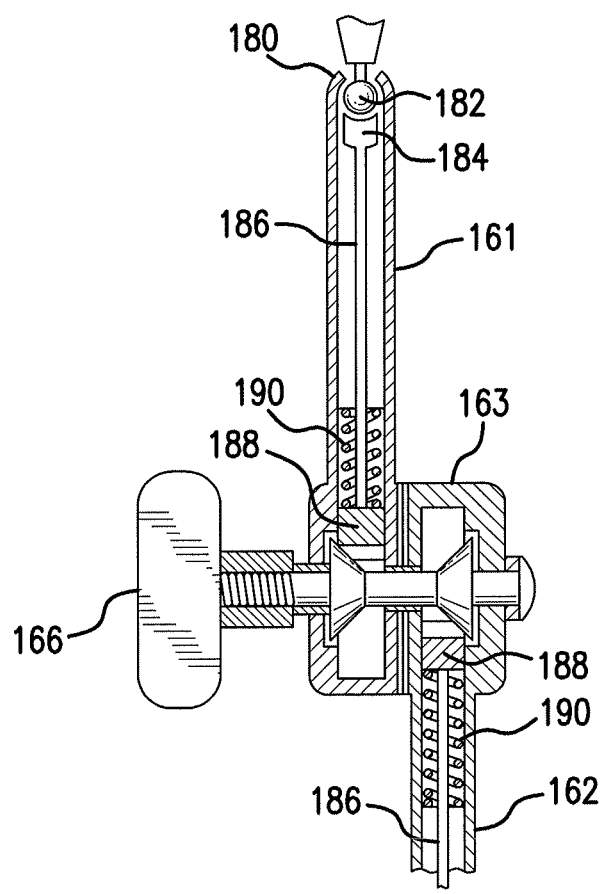

The bolts or pins 164*a,b* may be threaded to horizontal bar 120 and secondary adjustment member 140, as shown in FIGS. 14-16. This provides a secure and adjustable connection between the positioning joint 160 and the horizontal bar 120 and the secondary adjustment member 140. That is, both ends of the positioning joint 160 can be secured and adjusted in the manner as described with reference to FIG. 12 of U.S. Pat. No. 4,143,652, the contents of which have been incorporated by reference in their entirety (including, but not limited to, the description therein at col. 7, l. 18—col. 8, l. 9), or equivalent. FIG. 17 of the instant application, for example, depicts an exemplary embodiment for means of arresting or locking the positioning joint 160. As shown in FIG. 17, in the preferred embodiment, a pin joint or hinge 163 is arrange between two rods 161, 162. The one respective end of the rod 161, 162 possesses a flanged edge 180 (for illustrative purposes, only one flanged edge 180 is shown in FIG. 17), which engages about the associated ball 182. The ball 182 in turn rests in a socket 184 which is attached at one end of a thrust rod 186 which extends lengthwise through the rod 161. The other end of the thrust rod 186 is provided with a slide element or block 188 exposed to action of a pressure spring 190 supported in the rod 161, 162. The pressure spring 190 strives to shift the thrust rod 186 and together therewith the socket 184 from the flanged edge 180, and thereby releases the ball 182. to the extent visible in the showing of FIG. 17, the same components are provided in the rode 161 as in rod 162, and thus have been designated with the same reference characters.

In this manner, the presently disclosed telescoping surgical support and retractor system is provided with additional degrees of freedom by the positioning joint disposed between the horizontal bar 120 and the secondary adjustment member 140. In these embodiments, it may be possible to adjust the positioning of the surgical support and retractor systems with respect to the patient without having to move the system along the operating table rail 101, e.g., by the swinger clamp 102 as discussed above. Other benefits of this embodiment will be readily appreciated by those having ordinary skill in the art.

In a preferred embodiment of a surgical procedure using the inventive system, thyroid surgery is conducted, in which access to the thyroid is gained through the axilla. This procedure can be performed robotically or manually by a surgeon. The retractor used and the support can be configured to keep the surgical tool support as free from the tissue about the incision, such as an axillic incision, as possible to allow for other surgical equipment, which in some cases may be robotically operated, to more easily access the incision and thyroid or other tissue that needs to be accessed. Preferably, the surgical support system is easily adjustable to adapt it's position to a retractor that has already been positioned in an incision in a patient.

Using an embodiment including the position joint 160, the system is first roughly positioned over the operation area, with, for example, the swinger claim 102. Then, the positioning joint 160, operating turnkey 166, is adjusted to fine-tune the positioning of the system over the operation area. Then, the telescoping support members can be linearly adjusted as required for retraction in the surgery.

Further, the present application hereby incorporates by reference the entire contents of United States patent application publications 2006/0293568, filed Jun. 27, 2005 (application Ser. No. 11/166,170) and 2006/0290076, filed Jun. 24, 2005 (application Ser. No. 11/165,064). Additionally, the present application hereby incorporates by reference the entire contents of U.S. Pat. Nos. 4,796,846, 6,315,260, and 4,143,652.

The term "substantially," as used herein to refer to a shape, e.g., substantially semi-cylindrical or semi-circular cross-section, is intended to include variations from the true shape that do not affect the overall function of the device.

The term "about," as used herein, should generally be understood to refer to both numbers in a range of numerals. Moreover, all numerical ranges herein should be understood to include each whole integer within the range.

While illustrative embodiments of the invention are disclosed herein, it will be appreciated that numerous modifications and other embodiments can be devised by those of ordinary skill in the art. Features of the embodiments described herein can be combined, separated, interchanged, and/or rearranged to generate other embodiments. Therefore, it will be understood that the appended claims are intended to cover all such modifications and embodiments that come within the spirit and scope of the present invention.

What is claimed is:

1. A surgical support system, comprising:
a primary telescoping support that is linearly adjustable and includes a primary locking mechanism;
a secondary telescoping support that is linearly adjustable and includes a secondary locking mechanism and supported from the primary telescopic support and configured for telescopically mounting a surgical tool thereto, such that telescoping of the primary support repositions the secondary telescoping support;
a positioning joint disposed between the primary and secondary telescoping supports for universally positioning and locking the secondary telescoping support with respect to the primary telescoping support by locking the positioning joint; and
further comprising a base member including a rail clamp configured for securing the surgical support system selectively along a surgical table guide rail, wherein adjustment of the primary or secondary telescoping support allows movement in one direction without disengaging the primary or secondary locking mechanisms respectively but resists movement in the opposite direction until at least one of the primary or secondary locking mechanisms are disengaged, wherein at least one of the telescoping supports are adjusted by directly pulling on the at least one of the telescoping supports towards the rail clamp without disengaging the primary or secondary locking mechanism.

2. The surgical support system of claim 1, wherein the positioning joint comprises:
a first universally pivotable articulation connected to the primary telescopic support; and
a second articulation connected to the secondary telescoping support.

3. The surgical support system of claim 2, wherein the positioning joint comprises a plurality of articulations including the first and second articulations, first articulation being universally rotatable about an axis extending between the first articulation and an adjacent one of the plurality of articulations.

4. The surgical support system of claim of claim 3, wherein the positioning joint comprises a lock control that is manually operable to lock the plurality of articulations in a single operation.

5. The surgical support system of claim 2, wherein the first articulation is universally rotatable about an axis extending between the first and second articulations.

6. The surgical support system of claim 3, wherein the second articulation is universally pivotable.

7. The surgical support system of claim 6, wherein the positioning joint comprises a linking articulation connected between the first and second articulations.

8. The surgical support system of claim 7, wherein the linking articulation is a hinge articulation pivotable about a single axis.

9. The surgical support system of claim 8, wherein the axis of the hinge articulation is fixed with respect to the first and second articulations.

10. The surgical support system of claim 9, wherein the positioning joint comprises a lock control that is manually operable to lock in position the first, second, and linking articulations in a single operation.

11. The surgical support system of claim 10, wherein the positioning joint comprises rigid links connecting each adjacent articulation of the positioning joint.

12. The surgical support system of claim 1, wherein the positioning joint comprises:
a first articulation connected to the primary telescopic support; and
a second universally pivotable articulation connected to the secondary telescoping support.

13. The surgical support system of claim 7, wherein the first and second articulations are universally pivotable and rotatable about the linking articulation.

14. The surgical support system of claim 13, wherein the first and second articulations comprise of a ball-and-socket joint.

15. The surgical support system of claim 14, wherein the joint comprises a lock control to selectively lock and unlock the ball-and-sockets and the hinge in a single operation.

16. The surgical support system of claim 1, wherein the secondary telescoping support comprises a ratchet to adjustably engage a rack of a retractor.

17. The surgical support system of claim 1, wherein the primary telescoping support comprises:
a ratchet; and
a rack in telescoping association with respect to the ratchet, wherein the ratchet ratchets the rack to permit telescopic retraction of the rack and to prevent telescopic extension of the rack.

18. A surgical support system, comprising:
a primary telescoping support that is linearly adjustable and includes a primary locking mechanism;
a secondary telescoping support that is linearly adjustable and includes a secondary locking mechanism and supported from the primary telescopic support and configured for telescopically mounting a surgical tool thereto, such that telescoping of the primary support repositions the secondary telescoping support;
a positioning joint comprising:
  a first universal articulation connected to the primary telescoping support;
  a second universal articulation connected to the secondary telescoping support; and
  a lock control that is manually operable to lock the articulations in a single operation, and
further comprising a base member including a rail clamp configured for securing the surgical support system selectively along a surgical table guide rail, wherein adjustment of the primary or secondary telescoping support allows movement in one direction without disengaging the primary or secondary locking mechanisms respectively but resists movement in the opposite direction until at least one of the primary or secondary locking mechanisms are disengaged, wherein at least one of the telescoping supports are adjusted by directly puffing on the at least one of the telescoping supports towards the rail clamp without disengaging the primary or secondary locking mechanism.

* * * * *